United States Patent
Chan et al.

(10) Patent No.: US 10,085,889 B2
(45) Date of Patent: Oct. 2, 2018

(54) SYSTEM AND METHOD FOR TREATMENT OF EUSTACHIAN TUBE FROM ORAL APPROACH

(71) Applicant: Acclarent, Inc., Menlo Park, CA (US)

(72) Inventors: Randy S. Chan, San Jose, CA (US); Ketan P. Muni, San Jose, CA (US); Hung V. Ha, San Jose, CA (US); Andy Nguyen, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 392 days.

(21) Appl. No.: 14/928,151

(22) Filed: Oct. 30, 2015

(65) Prior Publication Data

US 2017/0119582 A1    May 4, 2017

(51) Int. Cl.
| | | |
|---|---|---|
| *A61F 11/00* | (2006.01) | |
| *A61M 31/00* | (2006.01) | |
| *A61M 29/02* | (2006.01) | |
| *A61M 25/10* | (2013.01) | |
| *A61B 17/24* | (2006.01) | |
| *A61M 25/09* | (2006.01) | |

(Continued)

(52) U.S. Cl.
CPC ............ *A61F 11/002* (2013.01); *A61B 1/227* (2013.01); *A61B 17/24* (2013.01); *A61M 5/007* (2013.01); *A61M 19/00* (2013.01); *A61M 25/09* (2013.01); *A61M 25/10* (2013.01); *A61M 29/02* (2013.01); *A61M 31/00* (2013.01); *A61B 2017/00787* (2013.01); *A61M 2029/025* (2013.01); *A61M 2210/0675* (2013.01)

(58) Field of Classification Search
CPC ....... A61F 11/002; A61B 1/227; A61B 17/24; A61B 2017/00787; A61M 5/007; A61M 19/00; A61M 25/09; A61M 25/10; A61M 29/02; A61M 31/00; A61M 2029/025; A61M 2210/0675
USPC ......................................................... 604/514
See application file for complete search history.

(56) References Cited

U.S. PATENT DOCUMENTS 4,884,573 A * 12/1989 Wijay ..................... A61L 29/06
                                                          604/913
6,716,813 B2     4/2004 Lim et al.
(Continued)

OTHER PUBLICATIONS

International Search Report and Written Opinion dated Feb. 2, 2017 for Application No. PCT/US2016/058727, 10 pgs.

(Continued)

*Primary Examiner* — Manuel Mendez
(74) *Attorney, Agent, or Firm* — Frost Brown Todd LLC

(57) ABSTRACT

A method of dilating a first Eustachian tube (ET) and a second ET of a patient using a dilation catheter includes directing the dilation catheter into the mouth of the patient and advancing the dilation catheter into a first ET on one side of the patient's head while a proximal portion of the dilation catheter is disposed in the mouth of the patient. The method further includes expanding the expandable member to thereby dilate the first ET. The method may further include repositioning the dilation catheter relative to a second ET on another side of the patient's head and advancing the dilation catheter into the second ET while a proximal portion of the dilation catheter is disposed in the mouth of the patient. The method may further include expanding the expandable member to thereby dilate the second ET.

20 Claims, 13 Drawing Sheets

(51) Int. Cl.
*A61B 1/227* (2006.01)
*A61M 5/00* (2006.01)
*A61M 19/00* (2006.01)
*A61B 17/00* (2006.01)

(56) References Cited

U.S. PATENT DOCUMENTS

| | | | |
|---|---|---|---|
| 2007/0264310 A1* | 11/2007 | Hissong | A61F 11/002 |
| | | | 424/437 |
| 2008/0154343 A1* | 6/2008 | Li | A61B 18/22 |
| | | | 607/89 |
| 2010/0030031 A1 | 2/2010 | Goldfarb et al. | |
| 2010/0274188 A1 | 10/2010 | Chang et al. | |
| 2013/0172931 A1* | 7/2013 | Gross | A61F 5/566 |
| | | | 606/230 |
| 2013/0274715 A1 | 10/2013 | Chan et al. | |
| 2015/0374963 A1 | 12/2015 | Chan et al. | |

OTHER PUBLICATIONS

St. Croix, B., et al., "Genes Expressed in Human Tumor Endothelium," Science, Aug. 18, 2000, 289:1197-1202, 6 pgs.
U.S. Appl. No. 62/139,919, filed Mar. 30, 2015.

* cited by examiner

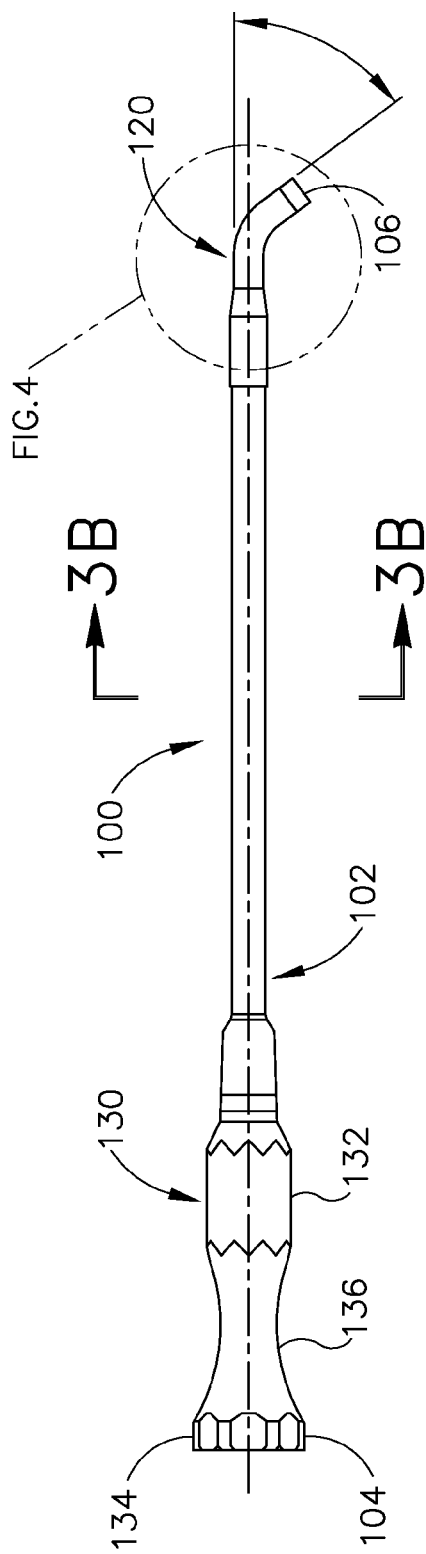
Fig.3A
Fig.3B
Fig.4

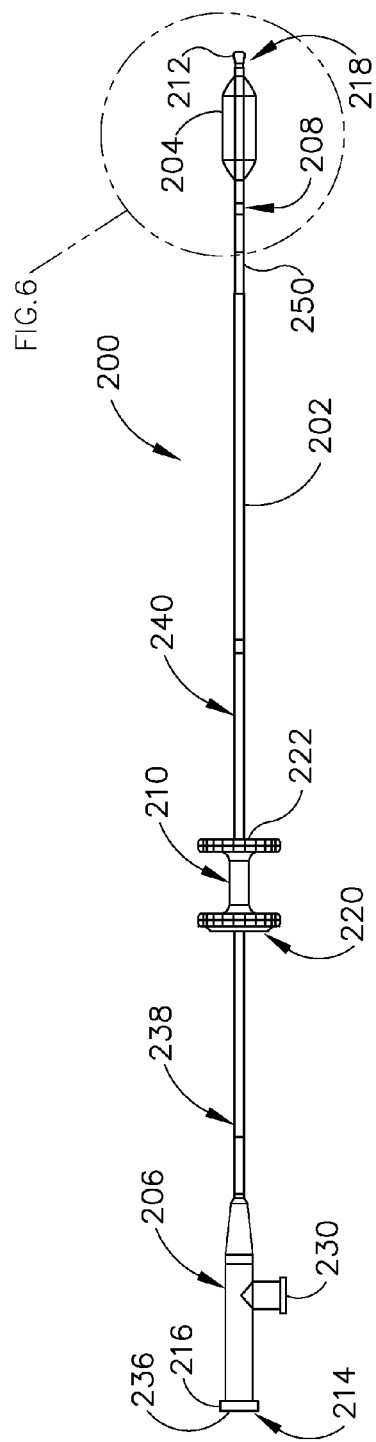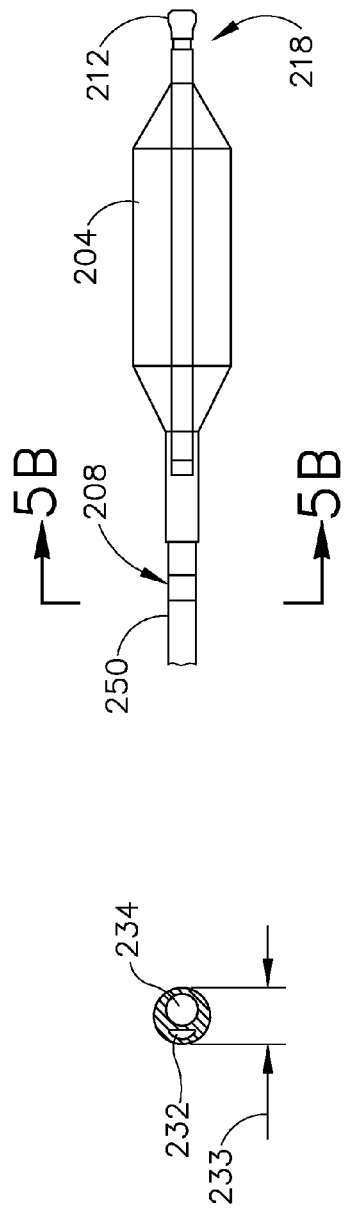
Fig.5A
Fig.5B
Fig.6

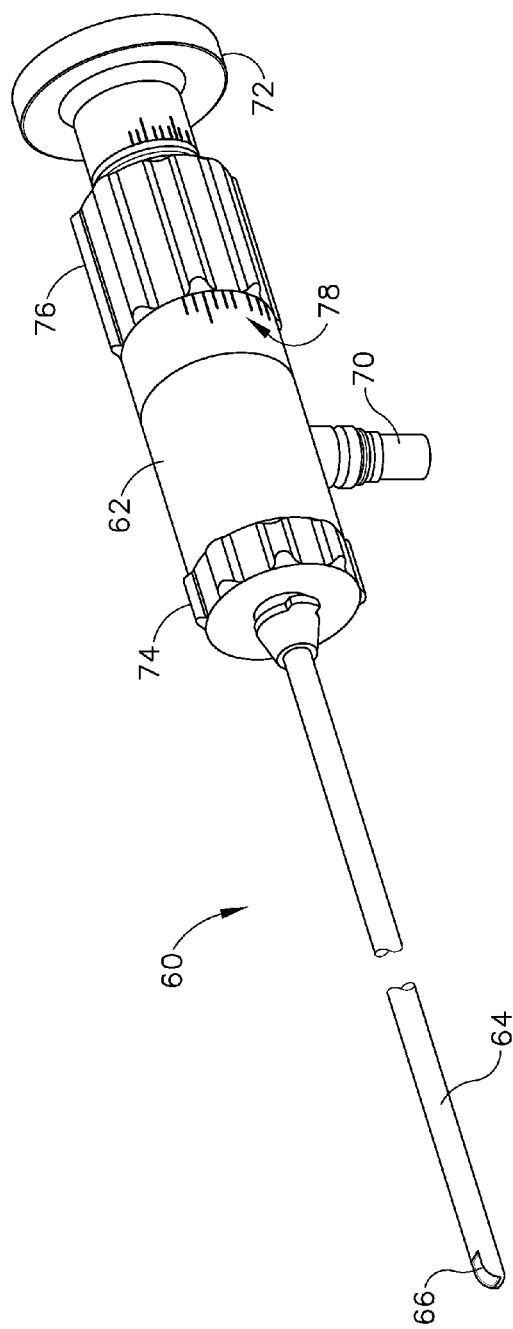
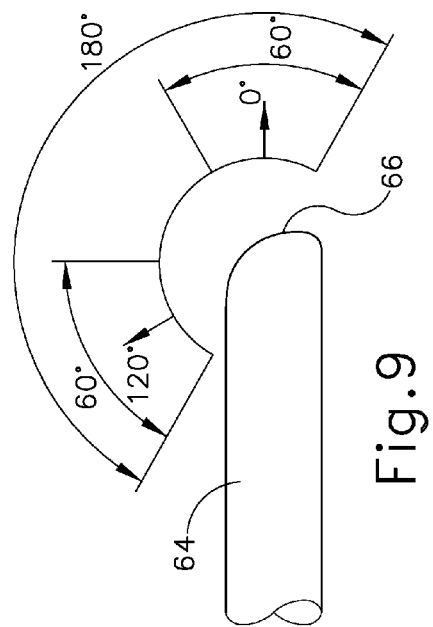
Fig. 8
Fig. 9

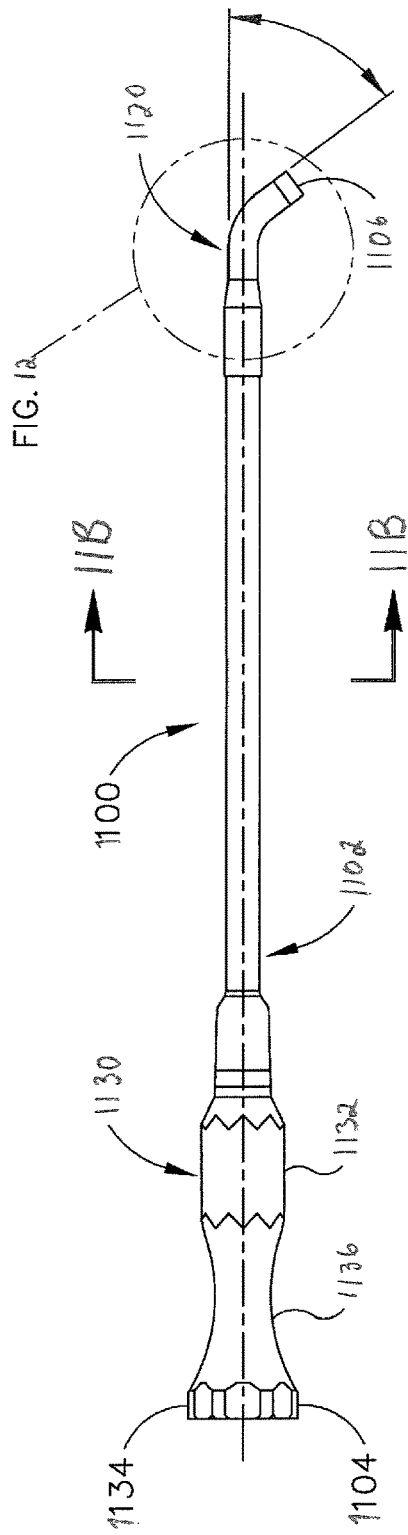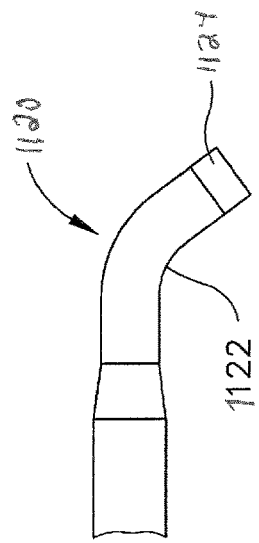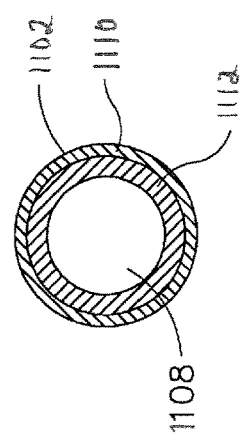
Fig. 11A
Fig. 12
Fig. 11B

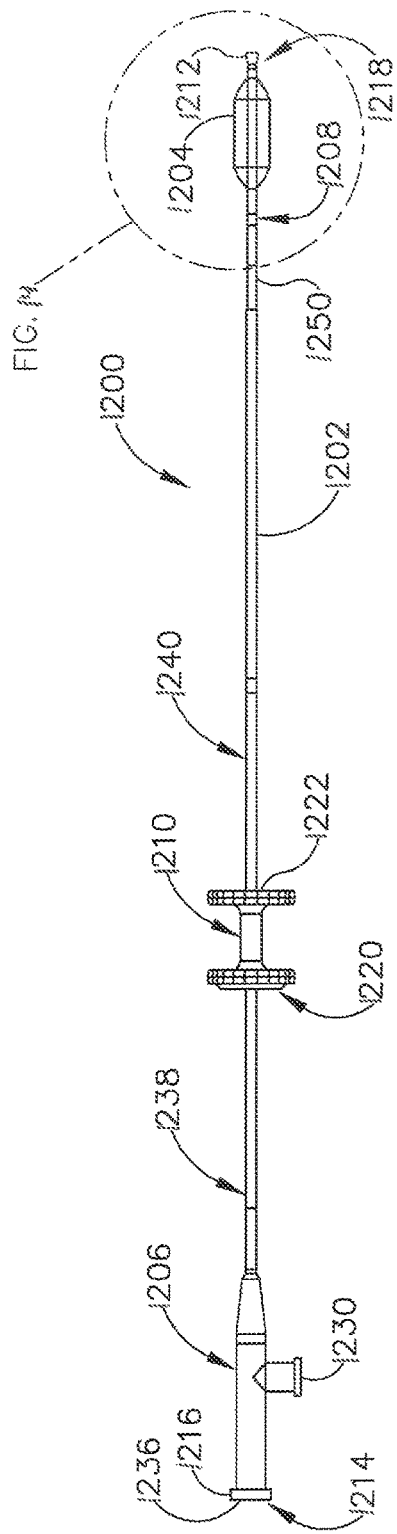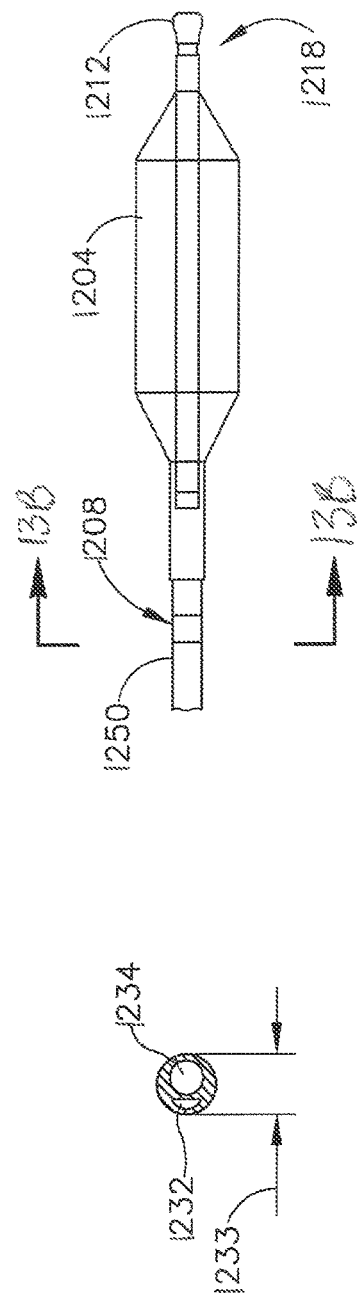

SYSTEM AND METHOD FOR TREATMENT OF EUSTACHIAN TUBE FROM ORAL APPROACH

BACKGROUND

Referring to FIGS. 1-2, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the sinuses. The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (40) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. The ET (26) functions as a pressure equalizing valve for the middle ear (14), which is normally filled with air. When functioning properly, the ET (26) opens for a fraction of a second periodically (about once every three minutes) in response to swallowing or yawning. In so doing, it allows air into the middle ear (14) to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This occurs frequently in children in connection with an upper respiratory infection and accounts for the hearing impairment associated with this condition.

A lining membrane (mucous membrane) of the middle ear (14) and ET (26) is connected with, and is the same as, the membrane of the nose (42), sinuses (44) and throat (32). Infection of these areas results in mucous membrane swelling which in turn may result in obstruction of the ET (26). This is referred to as serous otitis media, which as discussed above is essentially a collection of fluid in the middle ear (14). Serous otitis media can be acute or chronic, and may be the result of blockage of the pharyngeal ostium (28) of the ET (26), which leads to the accumulation of fluid in the middle ear (14). In the presence of bacteria, this fluid may become infected, leading to an acute suppurative otitis media (infected or abscessed middle ear). When infection does not develop, the fluid remains until the ET (26) again begins to function normally, at which time the fluid is absorbed or drains down the tube into the throat (32) through the ET (26) pharyngeal ostium (28).

Chronic serous otitis media may result from longstanding ET blockage, or from thickening of the fluid so that it cannot be absorbed or drained down the ET (26). This chronic condition may lead to hearing impairment. There may be recurrent ear pain, especially when the individual catches a cold. Fortunately, serous otitis media may persist for many years without producing any permanent damage to the middle ear mechanism. The presence of fluid in the middle ear (14), however, makes it very susceptible to recurrent acute infections. These recurrent infections may result in middle ear damage.

When the ET (26) contains a build-up of fluid, a number of things may occur. First, the body may absorb the air from the middle ear (14), causing a vacuum to form that tends to pull the lining membrane and ear drum (22) inwardly, causing pain. Next, the body may replace the vacuum with more fluid which tends to relieve the pain, but the patient can experience a fullness sensation in the ear (10). Treatment of this condition with antihistamines and decongestants can take many weeks to be fully effective. Finally, the fluid can become infected, which can lead to pain, illness, and temporary hearing loss. If the inner ear (14) is affected, the patient may feel a spinning or turning sensation (vertigo). The infection may be treated with antibiotics.

However, even if antihistamines, decongestants, and antibiotics are used to treat an infection or other cause of fluid build-up in the middle ear (14), these treatments may not immediately resolve the pain and discomfort caused by the buildup of fluid in the middle ear (14). The most immediate relief may be felt by the patient if the fluid can be removed from the ET (26).

Antibiotic treatment of middle ear infections may result in normal middle ear function within three to four weeks. During the healing period, the patient can experience varying degrees of ear pressure, popping, clicking and fluctuation of hearing, occasionally with shooting pain in the ear. Resolution of the infection may leave the patient with uninfected fluid in the middle ear (14), localized in the ET (26).

Fluid build-up caused by these types of infections may be treated surgically. The primary objective of surgical treatment of chronic serous otitis media may be to reestablish ventilation of the middle ear, keeping the hearing at a normal level and preventing recurrent infection that might damage the eardrum membrane and middle ear bones. One method to opening the ET (26) includes the "Valsalva" maneuver, accomplished by forcibly blowing air into the middle ear (14) while holding the nose, often called popping the ear. This method may be effective for opening the ET (26) but it may not clear the accumulated fluid from the middle ear (14) and is essentially a temporary fix when fluid is present in the middle ear (14).

Methods for treating the middle ear (14) and the ET (26) include those disclosed in U.S. Patent Pub. No. 2010/0274188, entitled "Method and System for Treating Target Tissue within the ET," published on Oct. 28, 2010, now abandoned, the disclosure of which is incorporated by reference herein; U.S. Patent Pub. No. 2013/0274715, entitled "Method and System for Eustachian Tube Dilation," published on Oct. 17, 2013, the disclosure of which is incorporated by reference herein; and U.S. Patent Pub. No. 2015/0374963, entitled "Vent Cap for a Eustachian Tube Dilation System," published on Dec. 31, 2015, the disclosure of which is incorporated by reference herein. As described in those references, functioning of the ET (26) may be improved by dilating the ET (26) with an expandable dilator instrument.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3A depicts a side elevational view of an exemplary guide catheter that may be used to position the dilation catheter of FIG. 5A.

FIG. 3B depicts a cross-sectional view of the guide catheter shown in FIG. 3A, taken along line 3B-3B of FIG. 3A.

FIG. 4 depicts an enlarged view of the distal end of the guide catheter shown in FIG. 3A.

FIG. 5A depicts a side elevational view of a balloon dilation catheter that may be used with the guide catheter of FIG. 3A.

FIG. 5B depicts a cross-sectional view of the balloon dilation catheter shown in FIG. 5A, taken along line 5B-5B of FIG. 6.

FIG. 6 depicts an enlarged view of the distal end of the balloon dilation catheter shown in FIG. 5A.

FIG. 8 depicts a perspective view of an exemplary endoscope suitable for use with the guide catheter of FIG. 3A and/or the balloon dilation catheter of FIG. 5A.

FIG. 9 depicts a side elevational view of the distal end of the endoscope of FIG. 8, showing an exemplary range of viewing angles.

FIG. 11A depicts a side elevational view of an exemplary alternative guide catheter that may be used to position the dilation catheter of FIG. 13A.

FIG. 11B depicts a cross-sectional view of the guide catheter of FIG. 11A, taken along line 11B-11B of FIG. 11A.

FIG. 12 depicts an enlarged view of the distal end of the guide catheter of FIG. 11A.

FIG. 13A depicts a side elevational view of a balloon dilation catheter that may be used with the guide catheter of FIG. 11A.

FIG. 13B depicts a cross-sectional view of the balloon dilation catheter shown in FIG. 13A, taken along line 13B-13B of FIG. 14.

FIG. 14 depicts an enlarged view of the distal end of the balloon dilation catheter shown in FIG. 13A.

DETAILED DESCRIPTION

Figure 1:
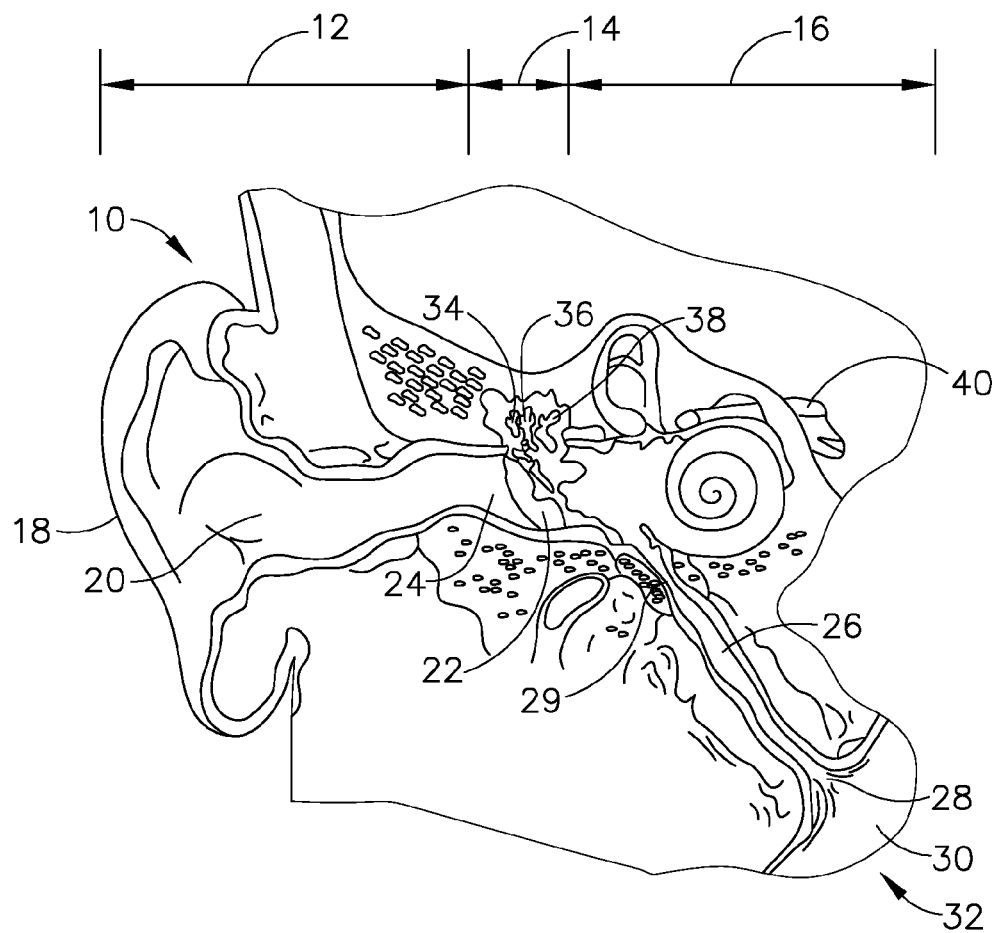
FIG. 1 depicts a cross-sectional view of a human ear showing the inner, middle and outer ear portions and the Eustachian tube connecting the middle ear with the nasopharynx region of the throat.
Figure 2:
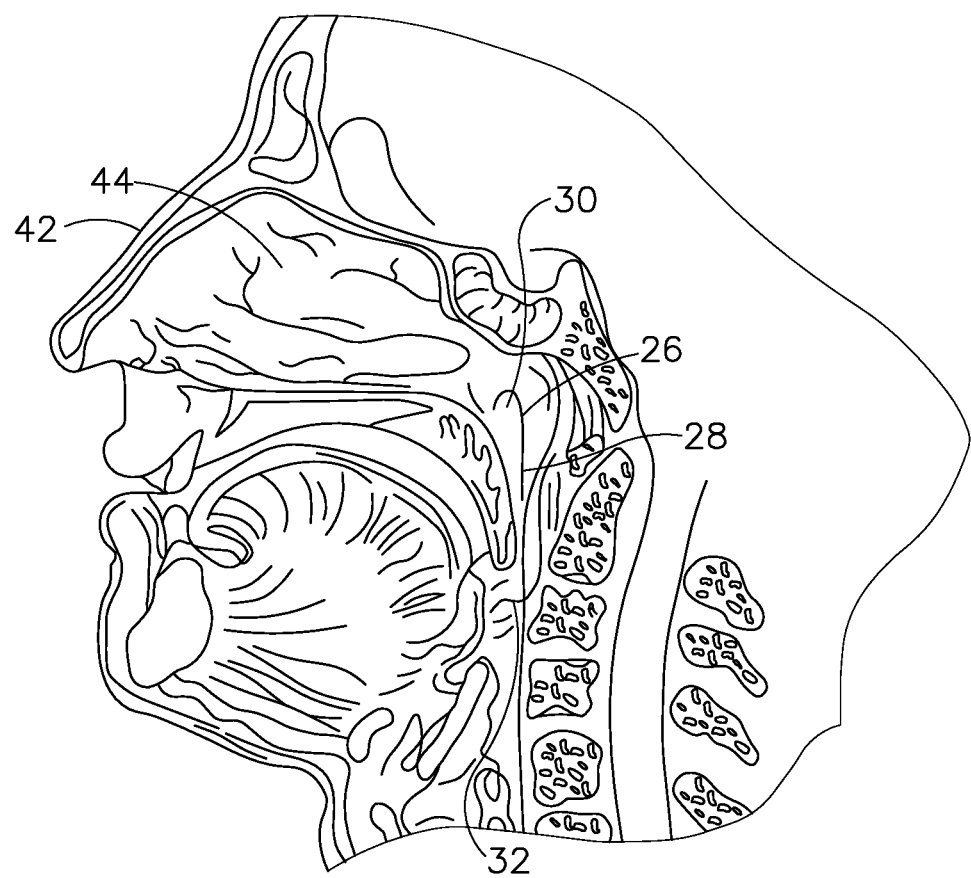
FIG. 2 depicts a cross-sectional view of a human head showing the nasopharynx region of the throat illustrated in FIG. 1 containing the pharyngeal ostium of the Eustachian tube illustrated in FIG. 1.

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

I. Exemplary Eustachian Tube Dilation Catheter System

One example of a treatment that may be performed to treat an ET (26) that does not provide sufficient communication between the middle ear (14) and the pharyngeal ostium (28) includes accessing and dilating the ET (26) using a guide catheter (100) and a balloon dilation catheter (200), examples of which are shown in FIGS. 3A-6. Guide catheter (100) of the present example includes an elongate tubular shaft (102) that has a proximal end (104), a distal end (106) and a lumen (108) therebetween. The guide catheter (100) may have any suitable length, diameter, angle of bend, and location of the bend along the length of the catheter (100), to facilitate accessing an ET (26) opening, such as the pharyngeal ostium (28). In some examples, the guide catheter (100) may have a length between about 8 cm and about 20 cm, or more particularly between about 10 cm and about 15 cm, or more particularly about 11 cm.

FIG. 3B is a cross-sectional view of the elongate tubular shaft (102) of guide catheter (100). As can be seen, shaft (102) has an outer shaft tube (110), an inner shaft tube (112) and a lumen (108). The outer shaft tube (110) may be constructed of a stiff material such as stainless steel and the inner shaft tube (112) may be constructed of a more flexible material such as a polymeric material including but not limited to nylon and further including a PTFE liner. The lumen (108) has a diameter of between about 2 mm and 3 mm, or more particularly between about 2.5 mm and about 2.6 mm, such that the balloon dilation catheter (200) can be easily inserted into the lumen (108) for dilation of the ET (26). The combination of guide catheter (100) and balloon catheter (200) may a compact system that is designed for a one-handed procedure. By "compact," it is intended that the length of the guide catheter shaft that is distal of the bend in the guide catheter is between about 0.5 and 2.0 about cm, in some versions between about 1 and about 2 cm, and in some versions about 1 cm. The compactness may help reduce interference with other instruments, such as an endoscope that may be used to help in visualizing the positioning of the system, as described below.

The distal portion (120) of guide catheter (100) is shown in an enlarged view in FIG. 4. The distal portion (120) of the guide catheter (100) may have a bend (122) with an angle between about 45 degrees and about 65 degrees, and more preferably between about 50 degrees and about 60 degrees, and particularly about 55 degrees, to facilitate access into the ET (26) via the pharyngeal ostium (28). The distal portion (120) of the guide catheter (100) is made of a transparent material such as a polymer including but not limited to nylon and PTFE such that balloon dilation catheter (200) is visible within the distal portion (120) and such that distal portion (120) is more flexible than the elongate shaft (102). The distal tip (124) of the distal portion (120) of the guide catheter (100) is made of PEBAX® (polyether block amide) such that it provides for atraumatic access to the ET (26), and may contain 20% barium sulfate or other similar radiopaque materials for visualizable access.

Referring again to FIG. 3A, the proximal portion (130) of guide catheter (100) includes a proximal hub (132) to aid in insertion of the balloon catheter into the ET (26). The hub (132) has a larger diameter proximal end (134) and a smaller diameter middle section (136) to facilitate stabilization of the guide catheter (100) in the nose, rotation of the guide catheter (100), and insertion of the balloon catheter (200) as will be described in further detail below. The hub (132) is ergonomically designed for insertion, location, and rotation through slight manipulations with one hand.

Balloon dilation catheter (200) of the present example is shown in FIG. 5A. The balloon dilation catheter (200) of the present example generally includes an elongate shaft (202) having a proximal end (214) and a distal end (218). The balloon dilation catheter (200) further includes a balloon (204) on the distal end (218) of the elongate shaft (202). The balloon (204) may be a polymer balloon (compliant, semi-compliant, or non-compliant). In some versions, the balloon (204) comprises a suitable non-compliant material such as but not limited to polyethylene terepthalate (PET), PEBAX® (polyether block amide), nylon or the like. The balloon catheter (200) may include any size of balloon including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm). The balloon dilation catheter (200) generally includes a proximally located connection (230) for inflating/activating the balloon (204) by communicating a pressurized medium (e.g., saline) to balloon (204).

Figure 10A:
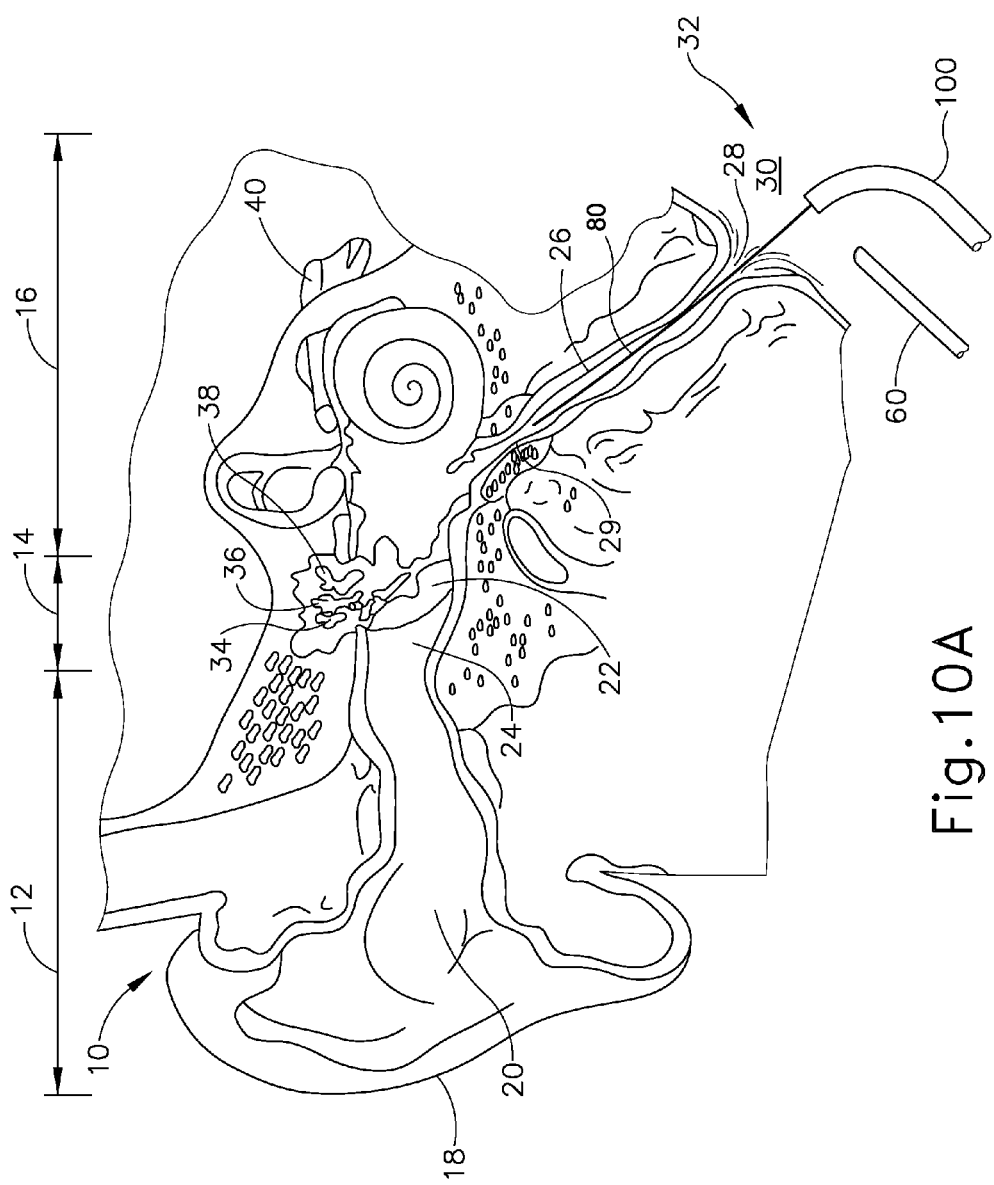
FIG. 10A depicts a cross-sectional view of a guide catheter, a balloon catheter, and an endoscope being positioned in relation to a Eustachian tube of a patient, with a guidewire disposed in the Eustachian tube.
Figure 10B:
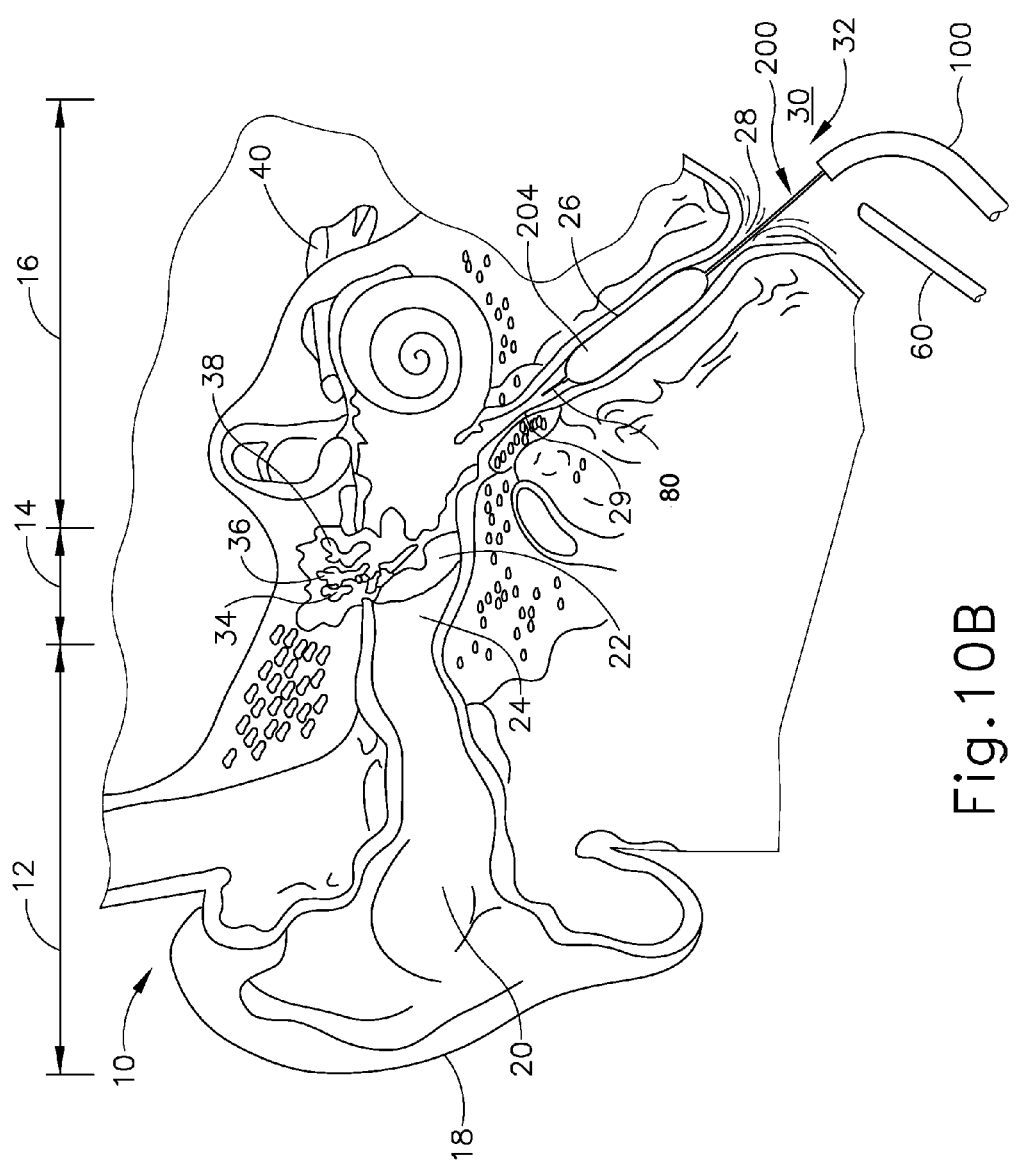
FIG. 10B depicts a cross-sectional view of the guide catheter, balloon catheter, and endoscope of FIG. 10A, with a balloon of the balloon catheter being expanded to dilate the Eustachian tube.

Balloon (204) may be expanded to dilate the ET (26) after balloon (204) is placed in a desirable location in the ET (26), as shown in FIGS. 10A-10B and described in greater detail below. For example, the opening area of the ET (26) includes a pharyngeal ostium (28), and dilation catheter (200) may be advanced to position the balloon in the pharyngeal ostium (28). An endoscope, such as endoscope (60) (FIGS. 8-9), may be used to assist in positioning the dilation catheter (200). Endoscope (60) may be advanced through the nasal passage to view the dilation catheter (200). A marker (208) on a shaft of the dilation catheter (200) can be viewed from endoscope (60) to approximate a location of the balloon (204) relative to the opening of the ET (26) (e.g., pharyngeal ostium (28)) based on a distance of the marker (208) from a proximal end of the balloon (204). Accordingly, dilation catheter (200) can be moved to place marker (208) in a desirable location before expansion of the balloon (204) in the ET (26).

Balloon dilation catheter (200) further includes an actuator (210). Actuator (210) has a proximal side 220 and a distal side (222). In the example shown in FIG. 5A, actuator (210) is secured by an adhesive to elongate shaft (202). The portion (240) of elongate shaft (202) that is distal of actuator (210) is sufficiently stiff to be guided through the nasal cavity and into the ET (26) and is constructed of stainless steel and preferably includes a stainless steel hypotube. The portion (238) of elongate shaft (202) that is proximal of actuator (210) and the portion (250) that is distal to portion (240) is more flexible than the portion (240) and is constructed of a polymeric material including but not limited to PEBAX® (polyether block amide). In this way, proximal portion (238) of elongate shaft (202) will not interfere with the endoscope (60) described above as it is advanced through the nasal passage, such that the dilation catheter (200) can be easily viewed. The actuator (210) allows for easy, ergonomic one-handed advancement of dilation catheter (200) through guide catheter (100) and into the ET (26). Actuator (210) may be used to advance or retract in alternative ways including but not limited to use of the thumb, the index finger, or a combination of fingers (e.g., the index and middle fingers) or the thumb and the index or middle finger.

The distal end (218) of balloon catheter (200) further includes a tip (212) and a flexible shaft portion (250) that is constructed of a polymeric material including but not limited to PEBAX® (polyether block amide) that extends from the distal end of the elongate shaft (202) to the proximal end of balloon (204). In the example shown in FIG. 5A, tip (212) is a bulbous polymeric blueberry shaped, atraumatic tip and is about 1.5 mm to about 2 mm in length, with an outer diameter of between about 2 mm and about 3 mm. The smoothness and roundness of tip (212) facilitates advancement of the balloon catheter (200) by helping it glide smoothly through the ET (26). Tip (212) further acts as a safety stop. The isthmus (29) of the ET (26), shown in FIG. 1 is approximately 1 mm in diameter. The tip (212) diameter is larger than the outer diameter (233) of the elongate shaft (202) shown in cross-section in FIG. 5B such that the tip (212) size will prevent the balloon catheter (200) from passing through the isthmus (29) into the middle ear (14).

After balloon (204) is positioned within the ET (26) and inflated to an expanded state (e.g., as shown in FIG. 10B), balloon (204) may be held in location while in an expanded state for an extended period of time (e.g. several seconds or minutes). The balloon catheter (200) may also deliver a substance to the ET (26), such as one or more of the therapeutic or diagnostic agents described herein. Balloon (204) may also carry an expandable stent for delivery into the ET (26) upon expansion of balloon (204). Balloon dilation catheter (200) and guide catheter (100) may be removed from the patient after balloon (204) has been deflated/unexpanded. The ET (26) will resume functioning, normally opening and closing to equalize atmospheric pressure in the middle ear (14) and protect the middle ear (14) from unwanted pressure fluctuations and loud sounds.

Figure 7:
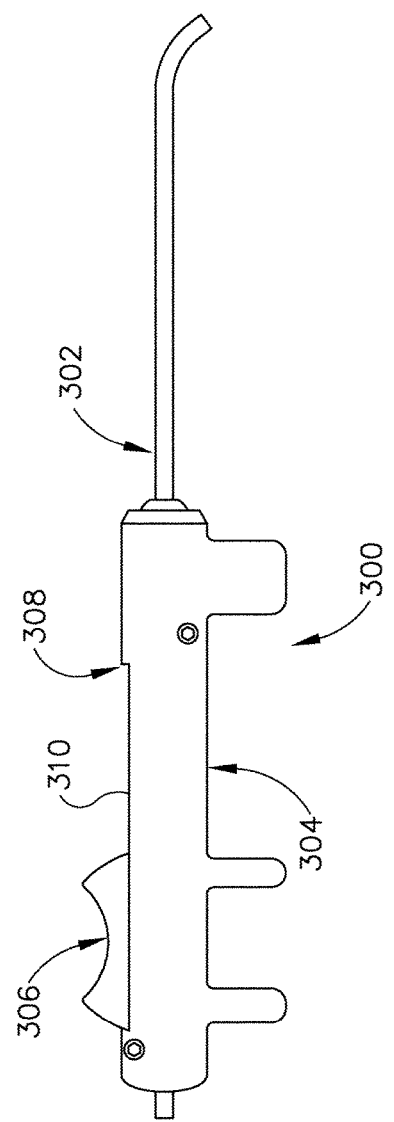
FIG. 7 depicts a side elevational view of another exemplary guide catheter that may be used to position the dilation catheter of FIG. 5A.

Another exemplary guide catheter (300) is shown in FIG. 7. In this example, proximal hub (132) is replaced with a handle (304). Guide catheter (300) comprises an elongate shaft (302) and a handle (304) to aid in insertion of a balloon catheter, such as balloon catheter (200), into the ET (26) in a manner similar to that described below with regard to the guide catheter (200). In the example shown in FIG. 7, an actuator (306) in the form of a slider is attached to portion of balloon catheter (200) that is contained within handle (304) and is slidably contained within elongate shaft (302) of guide catheter (300). Actuator (306) is thus slidable relative to handle (304) along a channel (310) to thereby selectively advance and retract balloon catheter (200) relative to elongate shaft (302). In use, elongate shaft (302) is inserted into the paranasal cavity of the patient and balloon catheter (200) is advanced into the ET (26) via thumb or single finger advancement of actuator (302) along channel (310) of handle (304). The advancement of balloon catheter (200) is continued until a visual marker indicates that advancement is complete, or until the enlarged tip (212) of balloon catheter (200) abuts the isthmus of the ET (26); or actuator (302) abuts the distal end (308) of channel (310) in handle (304) and is therefore fully deployed.

II. Exemplary Endoscope

Referring to FIGS. 8-9, an endoscope (60) may be used to provide visualization within an anatomical passageway (e.g., within the oro-nasal cavity, etc.) during the process using guide catheter (100) and/or balloon catheter (200) just described, for example. Endoscope (62) of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

As noted above, an endoscope (60) may be used to provide visualization within an anatomical passageway (e.g., within the nasal cavity, etc.) during a process of using dilation catheter system, which in one example includes the balloon dilation catheter (200, 300) and, optionally, guide catheter (100). As shown in FIGS. 8-9, endoscope (60) of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Method of Treating the Eustachian Tube FIGS. 10A-10B show schematic versions of the guide catheter (100) and balloon catheter (200) being used to treat the ET (26) under visual guidance using endoscope (60). In use, guide catheter (100) may be advanced into a nostril and through a nasal cavity to position a distal end of the catheter (100) at, in or near the pharyngeal ostium (28), which opens into the ET (26). In some instances, the guide catheter (100) may be passed through a nostril to the ET (26) on the ipsilateral (same side) of the head. In some other instances, the guide catheter (100) may be passed through a nostril to the ET (26) on the contralateral (opposite side) of the head. A guiding element such as a guidewire (80) or illuminating fiber may be used to aid in accessing the ET (26). In some versions, guidewire (80) is omitted.

As shown in FIG. 10B, after guide catheter (100) is in a desired position, balloon catheter (200) is advanced through the guide catheter (100) to position balloon (204) of balloon catheter (200) within the ET (26). The physician/user may place the index and middle fingers on either side of the smaller diameter middle section (136) of proximal hub (132) of guide catheter (100). The physician/user will then place the thumb on the proximal side (220) of actuator (210) or within both sides of the actuator (210) and will use the thumb to slide the balloon dilation catheter (200) through guide catheter (100) to position balloon (204) within the ET (26). Alternatively, the user may grasp proximal hub (132)

of guide catheter (100) and use the index finger placed on the proximal side (220) of actuator (210) or in between the distal side (222) and the proximal side (220) of actuator (210) to advance balloon catheter (200). The larger diameter tip (212) prevents balloon catheter (200) from advancing past the isthmus (29) and into the middle ear (14). Further, distal side (222) of actuator (210) will bottom out against proximal end (104) of guide catheter (100), such that the balloon catheter (200) cannot advance any further. The actuator (210) thus prevents the balloon catheter (200) from reaching passing the isthmus (29) and reaching the middle ear (14). Further, actuator (210) can be positioned at the appropriate distance along the elongate shaft (202) such that access to the ET (26) may be from the contralateral or the ipsilateral side.

In an alternative example, a balloon catheter (200) is advanced into a nostril of a patient without the use of a guide catheter (100). The balloon (204) of the balloon catheter (200) is placed within the ET (26). The physician/user will advance the balloon catheter (200) until the proximal side (220) of the actuator (210) is adjacent the patient's nostril. The distal side (222) of the actuator (210) will bottom out against the patient's nostril, such that the balloon catheter cannot advance any further. The actuator (210) prevents the catheter from passing the isthmus (29) and reaching the middle ear (14). Further, actuator (210) can be positioned at the appropriate distance along the elongate shaft (202) such that access to the ET (26) may be from the contralateral or the ipsilateral side.

Any number of procedures may be carried out following placement of the balloon catheter (200) into the desired position as described above. For instance, the Eustachian tube (ET) may be dilated by communicating fluid to balloon (204) and thereby inflating balloon (204), in accordance with the teachings of various reference cited herein or otherwise. In addition or in the alternative, the isthmus (29) may be cleaned and/or otherwise treated as described in U.S. Patent Application No. 62/139,919, entitled "Method and Apparatus for Cleaning Isthmus of Eustachian Tube," filed Mar. 30, 2015, the disclosure of which is incorporated by reference herein.

The elongate shaft (202) contains adjacent dual lumen (232, 234) tubing (see FIG. 5B). By adjacent dual lumen tubing, it is intended that the lumens (232, 234) are next to each other but are spaced apart, one from the other. The inflation lumen (232) is used for inflation of the balloon (204) with water, contrast medium, or saline through inflation port (230) to a pressure of between about 3 and about 15 atmospheres, or of between about 6 and about 12 atmospheres. The injection lumen (234) permits the optional injection of water, medicament, or even the introduction of a guidewire (80) through the injection port (236) at the proximal end (216) of the proximal connector (206). In order to ensure that inflation port (230) is used for balloon (204) inflation only, inflation port (230) and injection port (236) may optionally have different type connectors. For example, inflation port (230) may be a female connector whereas injection port (236) is a male connector or vice versa. Alternatively, injection port (236) may have a right-handed thread connector and inflation port (230) may have a left-handed thread connector or vice versa.

It may be desirable to inject solutions containing contrast agents, pharmaceutically acceptable salt or dosage form of an antimicrobial agent (e.g. antibiotic, antiviral, anti-parasitic, antifungal, etc.), an anesthetic agent with or without a vasoconstriction agent (e.g. Xylocaine with or without epinephrine, Tetracaine with or without epinephrine, etc.), an analgesic agent, a corticosteroid or other anti-inflammatory (e.g. an NSAID), a decongestant (e.g. vasoconstrictor), a mucus thinning agent (e.g. an expectorant or mucolytic), a surfactant, an agent that prevents or modifies an allergic response (e.g. an antihistamine, cytokine inhibitor, leucotriene inhibitor, IgE inhibitor, immunomodulator), an allergen or another substance that causes secretion of mucous by tissues, hemostatic agents to stop bleeding, antiproliferative agents, cytotoxic agents (e.g. alcohol), biological agents such as protein molecules, stem cells, genes or gene therapy preparations, or the like.

Some nonlimiting examples of antimicrobial agents that may be used in this invention include acyclovir, amantadine, aminoglycosides (e.g., amikacin, gentamicin and tobramycin), amoxicillin, amoxicillinlclavulanate, amphotericin B, ampicillin, ampicillinlsulbactam, atovaquone, azithromycin, cefazolin, cefepime, cefotaxime, cefotetan, cefpodoxime, ceflazidime, ceflizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscamet, ganciclovir, atifloxacin, imipenemlcilastatin, isoniazid, itraconazole, ketoconazole, metronidazole, nafcillin, nafcillin, nystatin, penicillin, penicillin G, pentamidine, pip eracillinltazobactam, rifampin, quinupristindalfopristin, ticarcillinlclavulanate, trimethoprimlsulfamethoxazole, valacyclovir, vancomycin, mafenide, silver sulfadiazine, mupirocin (e.g., Bactroban, Glaxo SmithKline, Research Triangle Park, N.C.), nystatin, triamcinolonelnystatin, clotrimazolelbetamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulphonated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acid form); non-pathogenic or "friendly" microbes that cause the production of hydrogen peroxide or other substances that kill or inhibit the growth of pathogenic microbes (e.g., lactobacillus); antimicrobial proteins or peptides such as those described in U.S. Pat. No. 6,716,813 (Lin et al.,) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. For example, corticosteroids that have previously administered by intranasal 10 administration may be used, such as beclomethasone (Vancenase® or Beconase), flunisolide (Nasalid®), fluticasone proprionate (Flonase®), triamcinolone acetonide (Nasacort®), budesonide (Rhinocort Aqua®), loterednol etabonate (Locort) and mometasone (Nasonex®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexarnethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as mmesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor) and d) SYK Kinase inhibitors such as an agent designated as "R-112," manufactured by Rigel Pharmaceuticals, Inc, South San Francisco, Calif.

Additionally or alternatively, in some applications, such as those where it is desired to shrink mucosal tissue, cause decongestion, or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine. In one particular example, the substance delivered by this invention comprises a combination of an anti-inflammatory agent (e.g. a steroid or an NSAID) and a mucolytic agent.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chroma) and nedocromil.

Additionally or alternatively, in some applications such as those where it is desired to prevent or inhibit the effect of histamine, the substances delivered in this invention may include various antihistamines such as azelastine (e.g., Astylin) diphenhydramine, loratidine, etc.

Additionally or alternatively, in some examples such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsinlLEDTA, hyaluronidase, and tosyllysylchloromethane (TLCM).

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other antitumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-I, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, 1MC-IC11, 1M862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmetteguerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogslcongeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired, cells that participate in or effect mucogenesis or ciliagenesis, etc.

In one example, a local anesthetic, such as Lidocaine is injected through the injection lumen (234) prior to dilation of the ET (26). The injection lumen (234) can be used for venting during dilation so that pressure in the middle ear (14) does not increase or decrease.

IV. Exemplary Alternative Balloon Catheter

In some instances, it may be difficult or impossible to access the ET (26) by inserting instruments through the nostril, into the oro-nasal cavity, and through the pharyngeal ostium, as shown in FIGS. 10A-10B. This may be due to the anatomical constraints of a patient or, in some instances, to the limitations of a particular practitioner's skill set. Moreover, where both of a patient's ETs (26) are defective and need treatment, utilizing the nostril or ear canal as an access point to each of the ETs (26) requires the operator to remove the instrument after operating on one ET (26) on one side of the patient's head, and re-insert the instrument into the other nostril to access the ET (26) on the other side of the patient's head. Therefore, in some instances, it may be more efficacious to access the ET (26) through the oral cavity, or the mouth (15), rather than the nasal cavity, especially in instances where both ETs (26) must be treated.

FIGS. 11A-14 show an exemplary alternative guide catheter (1100) and an exemplary alternative balloon dilation catheter (1200) that may be used together for accessing the ET (26) through a patient's mouth (15). Guide catheter (1100) of the present example includes an elongate tubular shaft (1102) that has a proximal end (1104), a distal end (1106) and a lumen (1108) therebetween. The guide catheter (1100) may have any suitable length, diameter, angle of bend, and location of the bend along the length of the catheter (1100), to facilitate accessing an ET (26) opening, such as the pharyngeal ostium (28), from a transoral approach. It should be understood that the size and configuration of guide catheter (1100) would be different from the size and configuration of guide catheter (100) described above since guide catheter (1100) is positioned from a transoral approach while guide catheter (100) Is positioned from a transnasal approach.

By way of example only, guide catheter (1100) may have a length between about 12 cm and about 19 cm, or more particularly between about 14 cm and about 17 cm, or more particularly about 15.5 cm. Alternatively, guide catheter (1100) may have a length of about 15.8 cm. By way of further example only, guide catheter (1100) may have a diameter between about 2.75 mm and about 3.75 mm, or more particularly between about 3 mm and about 3.5 mm, or more particularly about 3.3 mm. By way of further example only, guide catheter (1100) may have a bend angle between about 45° and about 65°, or more particularly between about 50° and about 60°, or more particularly about 55°.

FIG. 11B is a cross-sectional view of the elongate tubular shaft (1102) of guide catheter (1100). As can be seen, shaft (1102) has an outer shaft tube (1110), an inner shaft tube (1112) and a lumen (1108). The outer shaft tube (1110) may be constructed of a stiff material such as stainless steel and the inner shaft tube (1112) may be constructed of a more flexible material such as a polymeric material including but not limited to nylon and further including a PTFE liner. The lumen (1108) has a diameter of between about 2 mm and about 3 mm, or more particularly between about 2.4 mm and about 2.6 mm, or more particularly about 2.5 mm, such that the balloon dilation catheter (1200) can be easily inserted into the lumen (1108) for dilation of the ET (26). The combination of guide catheter (1100) and balloon catheter (1200) may comprise a compact system that is designed for a one-handed procedure. By "compact," it is intended that the length of the region of guide catheter shaft (1102) that is distal of the bend (1122) is between about 0.5 cm and about 2.0 cm, or more particularly between about 0.7 cm and about 1.7 cm, or more particularly about 1.0 cm. The compactness may help reduce interference with other instruments, such as an endoscope that may be used to help in visualizing the positioning of the system, as described below.

The distal portion (1120) of guide catheter (1100) is shown in an enlarged view in FIG. 4. As noted above, the distal portion (1120) of the guide catheter (1100) may have a bend (1122) with an angle between about 45° and about 65°, or more particularly between about 50° and about 60°, or more particularly about 55°. The distal portion (1120) of the guide catheter (1100) is made of a transparent material such as a polymer including but not limited to nylon and PTFE such that balloon dilation catheter (1200) is visible within the distal portion (1120) and such that distal portion (1120) is more flexible than the elongate shaft (1102). The distal tip (1124) of the distal portion (1120) of the guide catheter (1100) is made of PEBAX® (polyether block amide) such that it provides for atraumatic access to the ET (26), and may contain 20% barium sulfate or other similar radiopaque materials for visualizable access.

Referring again to FIG. 11A, the proximal portion (1130) of guide catheter (1100) includes a proximal hub (1132) to aid in insertion of the balloon catheter into the ET (26). The hub (1132) has a larger diameter proximal end (1134) and a smaller diameter middle section (1136) to facilitate stabilization of the guide catheter (1100) in the mouth (15), rotation of the guide catheter (1100), and insertion of the balloon catheter (1200) as will be described in further detail below. The hub (1132) is ergonomically designed for insertion, location, and rotation through slight manipulations with one hand.

FIG. 13A shows balloon dilation catheter (1200) of the present example. The balloon dilation catheter (1200) of the present example generally includes an elongate shaft (1202) having a proximal end (1214) and a distal end (1218). By way of example only, shaft (1202) may have a length between about 20 cm and about 40 cm, or more particularly between about 20 cm and about 30 cm, or more particularly about 26 cm. The balloon dilation catheter (1200) further includes a balloon (1204) on the distal end (1218) of the elongate shaft (1202). The balloon (1204) may be a polymer balloon (compliant, semi-compliant, or non-compliant). In some versions, the balloon (1204) comprises a suitable non-compliant material such as but not limited to polyethylene terephthalate (PET), PEBAX® (polyether block amide), nylon or the like. The balloon catheter (1200) may include any size of balloon including, but not limited to, balloons of 2 mm to 8 mm in diameter or of between about 5 mm and 6 mm (when inflated) and 12 mm to 24 mm in working length (e.g., 2 mm×12 mm, 3.5 mm×12 mm, 5 mm×16 mm, 5 mm×24 mm, 6 mm×16 mm, 6 mm×20 mm, 6 mm×24 mm, 7 mm×16 mm, or 7 mm×24 mm).

The balloon dilation catheter (1200) generally includes a proximally located connection (1230) for inflating/activating the balloon (1204) by communicating a pressurized medium (e.g., saline) to balloon (1204). Balloon (1204) may be expanded to dilate the ET (26) after balloon (1204) is placed in a desirable location in the ET (26), in a similar manner as shown in FIGS. 10A-10B and described in greater detail below with reference to FIGS. 16A-16B. For example, the opening area of the ET (26) includes a pharyngeal ostium (28), and dilation catheter (1200) may be advanced to position the balloon in the pharyngeal ostium (28). An endoscope, such as endoscope (60) (FIGS. 8-9), may be used to assist in positioning the dilation catheter (1200). Endoscope (60) may be advanced through the nasal passage to view the dilation catheter (1200). A marker (1208) on a shaft of the dilation catheter (1200) can be viewed from endoscope (60) to approximate a location of the balloon (1204) relative to the opening of the ET (26) (e.g., pharyngeal ostium (28)) based on a distance of the marker (1208) from a proximal end of the balloon (1204). Accordingly, dilation catheter (1200) can be moved to place marker (1208) in a desirable location before expansion of the balloon (1204) in the ET (26).

Balloon dilation catheter (1200) further includes an actuator (1210). Actuator (1210) has a proximal side (1220) and a distal side (1222). In the example shown in FIG. 13A, actuator (1210) is secured by an adhesive to elongate shaft (1202). The portion (1240) of elongate shaft (1202) that is distal of actuator (1210) is sufficiently stiff to be guided through the mouth (15) and into the ET (26) and is constructed of stainless steel and preferably includes a stainless steel hypotube. The portion (1238) of elongate shaft (1202) that is proximal of actuator (1210) and the portion (1250) that is distal to portion (1240) is more flexible than the portion (1240) and is constructed of a polymeric material including but not limited to PEBAX® (polyether block amide). In this way, proximal portion (1238) of elongate shaft (1202) will not interfere with the endoscope (60) described above as it is advanced through the mouth (15), such that the dilation catheter (1200) can be easily viewed. The actuator (1210) allows for easy, ergonomic one-handed advancement of dilation catheter (1200) through guide catheter (1100) and into the ET (26). Actuator (1210) may be used to advance or retract in alternative ways including but not limited to use of the thumb, the index finger, or a combination of fingers (e.g., the index and middle fingers) or the thumb and the index or middle finger.

The distal end (1218) of balloon catheter (1200) further includes a tip (1212) and a flexible shaft portion (1250) that is constructed of a polymeric material including but not limited to PEBAX® (polyether block amide) that extends from the distal end of the elongate shaft (1202) to the proximal end of balloon (1204). In the example shown in FIG. 13A, tip (1212) is a bulbous polymeric blueberry shaped, atraumatic tip and is about 1.5 mm to about 2 mm in length, with an outer diameter of between about 2 mm and about 3 mm. The smoothness and roundness of tip (1212) facilitates advancement of the balloon catheter (1200) by helping it glide smoothly through the ET (26). Tip (1212) further acts as a safety stop. The isthmus (29) of the ET (26), shown in FIG. 1 is approximately 1 mm in diameter. The tip (1212) diameter is larger than the outer diameter (1233) of the elongate shaft (1202) shown in cross-section in FIG. 13B such that the tip (1212) size will prevent the balloon catheter (1200) from passing through the isthmus (29) into the middle ear (14).

Figure 16A:
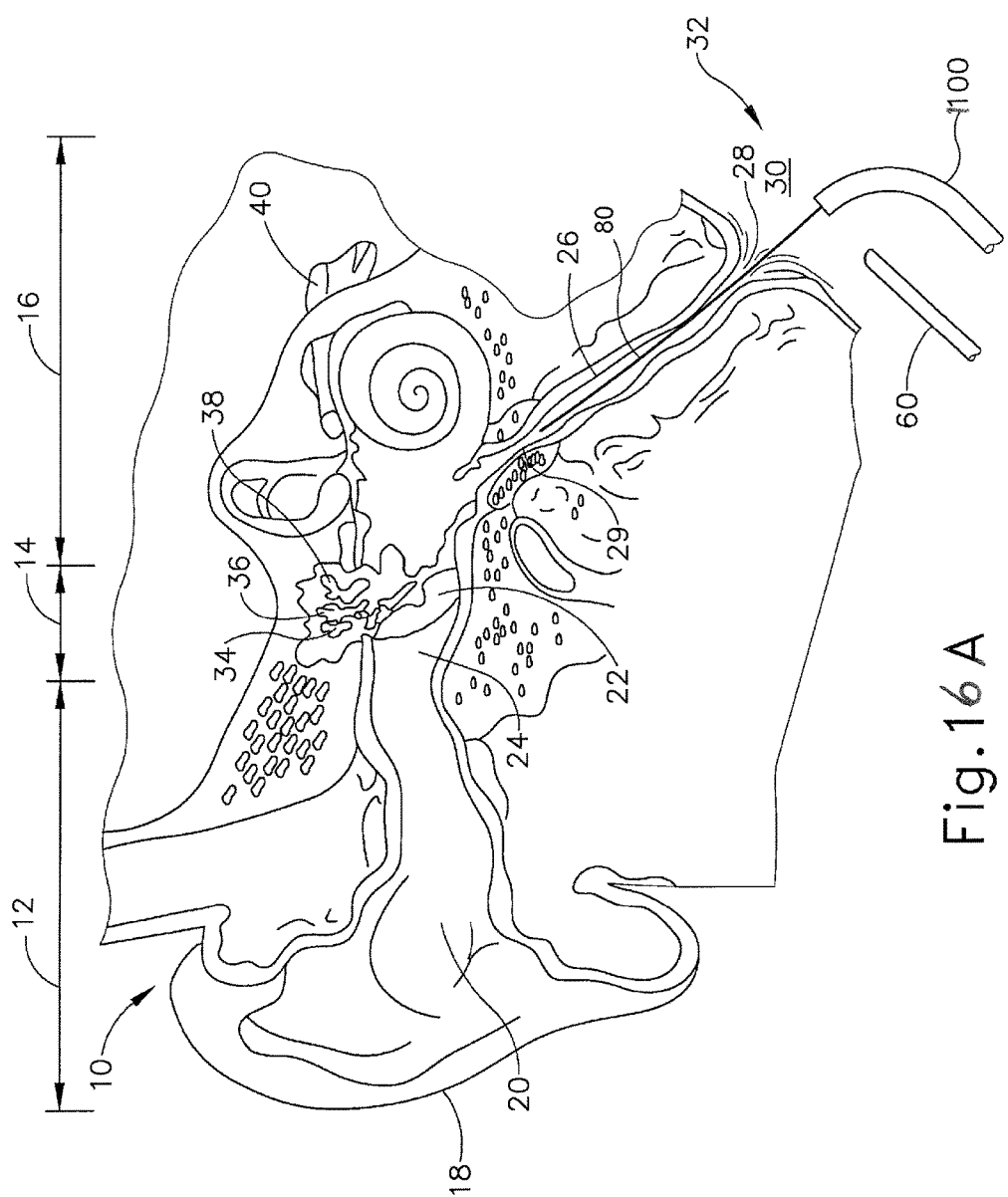
FIG. 16A depicts a cross-sectional view of the guide catheter of FIG. 11A, the balloon catheter of FIG. 13A, and an endoscope being positioned in relation to a Eustachian tube of a patient, with a guidewire disposed in the Eustachian tube.
Figure 16B:
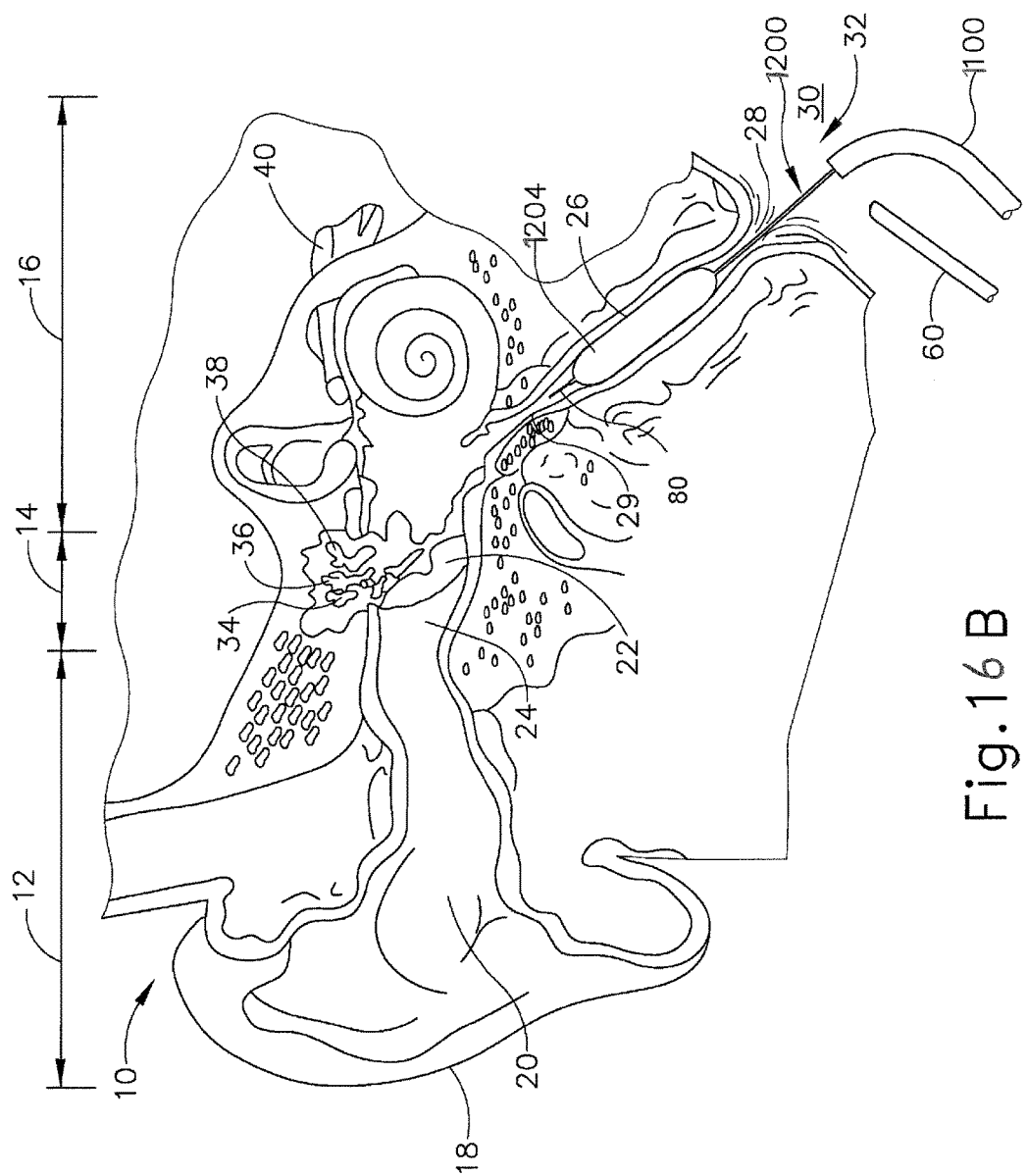
FIG. 16B depicts a cross-sectional view of the guide catheter of FIG. 11A, the balloon catheter of FIG. 13A, and the endoscope of FIG. 16A, with a balloon of the balloon catheter being expanded to dilate the Eustachian tube.

After balloon (1204) is positioned within the ET (26) and inflated to an expanded state (e.g., as shown in FIG. 16B), balloon (1204) may be held in location while in an expanded state for an extended period of time (e.g. several seconds or minutes). The balloon catheter (1200) may also deliver a substance to the ET (26), such as one or more of the therapeutic or diagnostic agents described herein. Balloon (1204) may also carry an expandable stent for delivery into the ET (26) upon expansion of balloon (1204). Balloon dilation catheter (1200) and guide catheter (1100) may be removed from the patient after balloon (1204) has been deflated/unexpanded. The ET (26) will resume functioning, normally opening and closing to equalize atmospheric pressure in the middle ear (14) and protect the middle ear (14) from unwanted pressure fluctuations and loud sounds.

Figure 15:
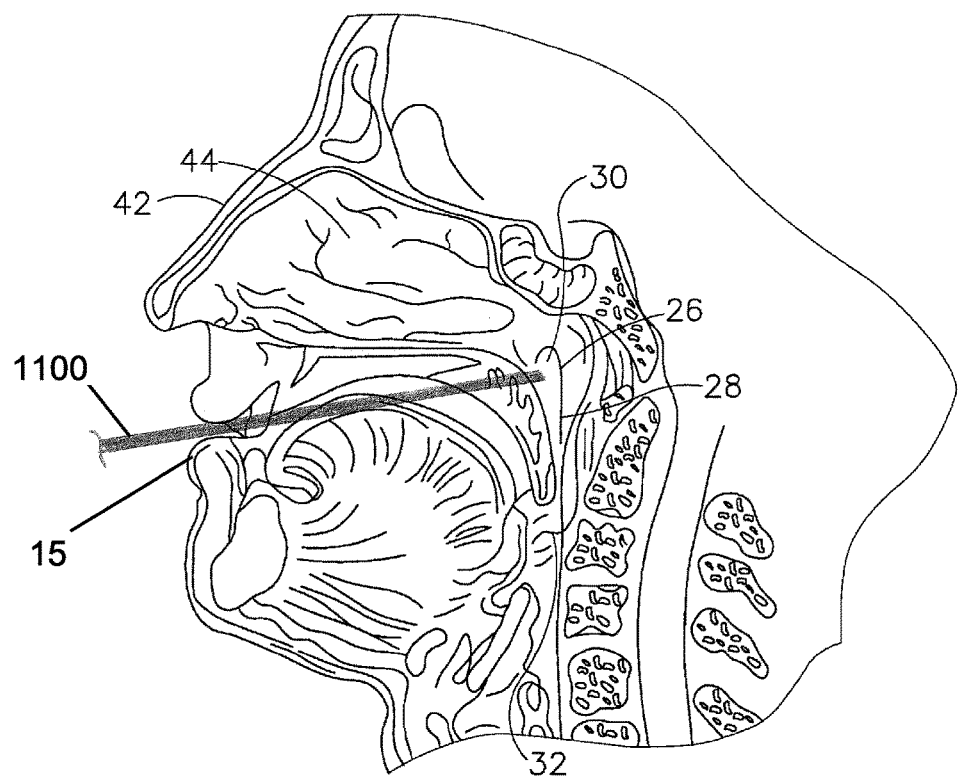
FIG. 15 depicts a schematic view of the guide catheter of FIG. 11A inserted into the mouth of a patient.

V. Exemplary Alternative Method of Treating the Eustachian Tube Via Oral Approach FIGS. 15-16B show schematic versions of the guide catheter (1100) and balloon catheter (1200) being used to treat the ET (26). Rather than advancing guide catheter (1100) and balloon catheter (1200) through a nostril, into the nasal cavity, and through the pharyngeal ostium (28), the method of the present example includes accessing the ET (26) through the mouth (15) and the pharyngeal ostium (28), as shown in FIG. 15. In some instances, the soft palate of the mouth (15) may be held open using an instrument such as a grasping tool or ties during performance of the method described below.

In some versions, guide catheter (1100) and balloon catheter (1200) are inserted together, as a unit, through the mouth (15) and into the oro-nasal cavity, with tip (1212) of balloon catheter (1200) being located at or proximal to distal tip (1124) of guide catheter (1100). In some other versions, guide catheter (1100) is first inserted through the mouth (15) and into the oro-nasal cavity; and then balloon catheter (1200) is inserted into guide catheter (1100) after guide catheter (1100) has been positioned in the mouth (15) and oro-nasal cavity. In either case, distal tip (1124) of guide catheter (1100) is eventually positioned at, in, or near the pharyngeal ostium (28), which opens into the ET (26). In the example shown in FIG. 16A, a guidewire (80) is advanced distally from guide catheter (1100) to enter the ET (26) via the pharyngeal ostium (28). In some other versions, guidewire (80) is omitted. As also shown in FIG. 16A, an endoscope (60) is used to provide visual guidance. Endoscope (60) may also be inserted through the mouth (15). Alternatively, endoscope (60) may be inserted through a nostril.

Once guide catheter (1100) has been suitably positioned in relation to the pharyngeal ostium (28), and particularly after guidewire (80) is positioned in the ET (26) via the pharyngeal ostium (28), balloon catheter (1200) is then advanced distally relative to guide catheter (1100) to position balloon (1204) in the ET (26). Once balloon (1204) is positioned in the ET (26), the operator may inflate the balloon (1204) to dilate the ET (26), as shown in FIG. 16B. Once the ET (26) is sufficiently dilated, balloon (1204) may be deflated, and balloon catheter (1200) may then be removed from the ET (26) and retracted relative to guide catheter (1100). In some instances, the other ET (26) may be dilated. In such instances, the guide catheter (1100) may be repositioned, without removing balloon catheter (1200) or guide catheter (1100) from the patient, to access the other pharyngeal ostium (28), which provides access to the other ET (26). The operator may advance balloon catheter (1200) relative to guide catheter (1100) and ET (26) such that balloon (1204) may be properly placed within the other ET (26) as discussed above. The operator may then inflate the balloon (1204) to dilate the other ET (26). Upon both ET(s) (26) being sufficiently dilated, the operator may remove the guide catheter (1100) and balloon catheter (1200) from the patient. Each ET (26) may then resume functioning, normally opening and closing to equalize atmospheric pressure in the middle ear (14) and protect the middle ear (14) from unwanted pressure fluctuations and loud sounds.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of dilating a first Eustachian tube (ET) of a patient using a dilation catheter, wherein the method comprises: (a) directing the dilation catheter into the mouth of the patient; (b) advancing the dilation catheter into a first ET on one side of the patient's head while a proximal portion of the dilation catheter is disposed in the mouth of the patient; and (c) expanding the expandable member to thereby dilate the first ET

Example 2

The method of Example 1, further comprising: (a) repositioning the dilation catheter relative to a second ET on another side of the patient's head while a proximal portion of the dilation catheter is disposed in the mouth of the patient; (b) advancing the dilation catheter into the second ET while a proximal portion of the dilation catheter is disposed in the mouth of the patient; and (c) expanding the expandable member to thereby dilate the second ET.

Example 3

The method of any one or more of Examples 1 through 2, further comprising: (a) directing a guide member into the mouth of the patient; and (b) advancing at least part of a distal portion of the guide member adjacent to an opening of a first ET on one side of the patient's head; wherein the act of advancing the dilation catheter comprises advancing the dilation catheter relative to the guide member, wherein the guide member directs the dilation catheter into the first ET during the act of advancing the dilation catheter relative to the guide member; wherein a proximal portion of the guide member is disposed in the mouth of the patient during the act of advancing the dilation catheter relative to the guide member.

Example 4

The method of Example 3, wherein the distal portion of the guide member comprises a bend.

Example 5

The method of Example 4, wherein the bend has a bend angle between about 45° and about 65°.

Example 6

The method of any one or more of Examples 3 through 5, wherein the guide catheter has a length between about 14 cm and about 17 cm.

Example 7

The method of any one or more of Examples 3 through 7, further comprising: (a) repositioning the guide catheter relative to a second ET on another side of the patient's head while a proximal portion of the guide catheter is disposed in the mouth of the patient; and (b) advancing the dilation catheter relative to the repositioned guide catheter to thereby drive the dilation catheter into the second ET while a proximal portion of the dilation catheter is disposed in the mouth of the patient.

Example 8

The method of any one or more of Examples 1 through 7, wherein the expandable member comprises an inflatable balloon, wherein the act of expanding the expandable member comprises inflating the balloon.

Example 9

The method of any one or more of Examples 1 through 8, wherein the expandable member comprises a mechanically expandable element, wherein the act of expanding the expandable member comprises expanding the expandable element.

Example 10

The method of any one or more of Examples 1 through 9, further comprising displacing a portion of a soft palate of the mouth.

Example 11

The method of Example 10, wherein displacing the portion of the soft palate comprises tying down the soft palate.

Example 12

The method of any one or more of Examples 1 through 11, further comprising delivering a therapeutic agent to the first ET.

Example 13

A method of dilating Eustachian tubes (ETs) of a patient using a dilation catheter, wherein the method comprises: (a) directing the dilation catheter into an oro-nasal cavity of the patient via the patient's mouth; (b) advancing the dilation catheter into a first ET of the patient; (c) expanding an expandable member of the dilation catheter to thereby dilate the first ET; (d) repositioning the dilation catheter toward a second ET of the patient without removing the dilation catheter from the oro-nasal cavity; (e) advancing the dilation catheter into the second ET; and (f) expanding the expandable member of the dilation catheter to thereby dilate the second ET.

Example 14

The method of Example 13, wherein the dilation catheter has a length of between about 20 cm and about 40 cm.

Example 15

The method of any one or more of Examples 13 through 14, wherein the dilation catheter comprises a shaft, wherein the shaft has a diameter between about 0.7 mm and about 1.1 mm.

Example 16

The method of any one or more of Examples 13 through 15, wherein steps (a) through (f) are all performed using a single hand.

Example 17

The method of any one or more of Examples 13 through 16, further directing a guide catheter into the oro-nasal cavity of the patient via the patient's mouth, wherein the act of advancing the dilation catheter comprises advancing the dilation catheter through the guide catheter.

Example 18

A method of dilating a Eustachian tube (ET) of a patient using a guide member and a dilation catheter, wherein the method comprises: (a) directing the guide member into a mouth of the patient; (b) directing the dilation catheter into the mouth of the patient via the guide member; (c) advancing at least part of a distal portion of the guide member adjacent to an opening of the ET while a proximal portion of the guide member remains disposed in the mouth of the patient, wherein the distal portion of the guide member has a bend; (d) advancing the dilation catheter relative to the guide member such that an expandable element of the dilation catheter is positioned distal to a distal end of the guide member and within the ET, wherein the bend of the guide member guides the expandable element into the ET as the dilation catheter is advanced relative to the guide member; and (e) expanding an expandable member of the dilation catheter to thereby dilate the ET.

Example 19

The method of Example 18, wherein advancing the dilation catheter relative to the guide member further comprises advancing the dilation catheter such that a predetermined length of the dilation catheter extends distally out of the guide catheter.

Example 20

The method of any one or more of Examples 18 through 19, further comprising advancing a guidewire relative to the guide member such that a distal portion of the guidewire is positioned distal to a distal end of the guide member and within the ET, wherein the bend of the guide member guides the guidewire into the ET as the guidewire is advanced relative to the guide member, wherein the act of advancing the dilation catheter relative to the guide member comprises advancing the dilation catheter along the advanced guidewire.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of dilating a first Eustachian tube (ET) of a patient using a dilation catheter, wherein the method comprises:
   (a) directing the dilation catheter into the mouth of the patient;
   (b) advancing the dilation catheter into a first ET on one side of the patient's head while a proximal portion of the dilation catheter is disposed in the mouth of the patient; and
   (c) expanding an expandable member uniformly in a radial direction to thereby dilate the first ET, wherein the circumference of the expandable member is in contact with the circumference of the first ET.

2. The method of claim 1, further comprising:
   (a) repositioning the dilation catheter relative to a second ET on another side of the patient's head while the proximal portion of the dilation catheter is disposed in the mouth of the patient;
   (b) advancing the dilation catheter into the second ET while the proximal portion of the dilation catheter is disposed in the mouth of the patient; and
   (c) expanding the expandable member to thereby dilate the second ET.

3. The method of claim 1, further comprising:
   (a) directing a guide member into the mouth of the patient; and
   (b) advancing at least part of a distal portion of the guide member adjacent to an opening of a first ET on one side of the patient's head;
   wherein the act of advancing the dilation catheter comprises advancing the dilation catheter relative to the guide member, wherein the guide member directs the dilation catheter into the first ET during the act of advancing the dilation catheter relative to the guide member;
   wherein a proximal portion of the guide member is disposed in the mouth of the patient during the act of advancing the dilation catheter relative to the guide member.

4. The method of claim 3, wherein the distal portion of the guide member comprises a bend.

5. The method of claim 4, wherein the bend has a bend angle between about 45° and about 65°.

6. The method of claim 3, wherein the guide catheter has a length between about 14 cm and about 17 cm.

7. The method of claim 3, further comprising:
   (a) repositioning the guide catheter relative to a second ET on another side of the patient's head while a proximal portion of the guide catheter is disposed in the mouth of the patient; and
   (b) advancing the dilation catheter relative to the repositioned guide catheter to thereby drive the dilation catheter into the second ET while a proximal portion of the dilation catheter is disposed in the mouth of the patient.

8. The method of claim 1, wherein the expandable member comprises an inflatable balloon, wherein the act of expanding the expandable member comprises inflating the balloon.

9. The method of claim 1, wherein the expandable member comprises a mechanically expandable element, wherein the act of expanding the expandable member comprises expanding the expandable element.

10. The method of claim 1, further comprising displacing a portion of a soft palate of the mouth.

11. The method of claim 10, wherein displacing the portion of the soft palate comprises tying down the soft palate.

12. The method of claim 1, further comprising delivering a therapeutic agent to the first ET.

13. A method of dilating Eustachian tubes (ETs) of a patient using a dilation catheter, wherein the method comprises:
   (a) directing the dilation catheter into an oro-nasal cavity of the patient via the patient's mouth;
   (b) advancing the dilation catheter into a first ET of the patient;
   (c) expanding an expandable member of the dilation catheter to thereby dilate the first ET;
   (d) repositioning the dilation catheter toward a second ET of the patient without removing the dilation catheter from the oro-nasal cavity;
   (e) advancing the dilation catheter into the second ET; and
   (f) expanding the expandable member of the dilation catheter to there by dilate the second ET.

14. The method of claim 13, wherein the dilation catheter has a length of between about 20 cm and about 40 cm.

15. The method of claim 13, wherein the dilation catheter comprises a shaft, wherein the shaft has a diameter between about 0.7 mm and about 1.1 mm.

16. The method of claim 13, wherein steps (a) through (f) are all performed using a single hand.

17. The method of claim 13, further directing a guide catheter into the oro-nasal cavity of the patient via the patient's mouth, wherein the act of advancing the dilation catheter comprises advancing the dilation catheter through the guide catheter.

18. A method of dilating a Eustachian tube (ET) of a patient using a guide member and a dilation catheter, wherein the method comprises:
   (a) directing the guide member into a mouth of the patient;
   (b) directing the dilation catheter into the mouth of the patient via the guide member;
   (c) advancing at least part of a distal portion of the guide member adjacent to an opening of the ET while a proximal portion of the guide member remains disposed in the mouth of the patient, wherein the distal portion of the guide member has a bend;
   (d) advancing the dilation catheter relative to the guide member such that an expandable element of the dilation catheter is positioned distal to a distal end of the guide member and within the ET, wherein the bend of the guide member guides the expandable element into the ET as the dilation catheter is advanced relative to the guide member; and
   (e) expanding the expandable element of the dilation catheter uniformly in a radial direction to thereby dilate the ET, wherein the circumference of the expandable element is in contact with the circumference of the ET.

19. The method of claim 18, wherein advancing the dilation catheter relative to the guide member further comprises advancing the dilation catheter such that a predetermined length of the dilation catheter extends distally out of the guide catheter.

20. The method of claim 18, further comprising advancing a guidewire relative to the guide member such that a distal portion of the guidewire is positioned distal to a distal end of the guide member and within the ET, wherein the bend of the guide member guides the guidewire into the ET as the guidewire is advanced relative to the guide member, wherein the act of advancing the dilation catheter relative to the guide member comprises advancing the dilation catheter along the advanced guidewire.

\* \* \* \* \*